(12) United States Patent
Polonka et al.

(10) Patent No.: US 8,206,691 B2
(45) Date of Patent: Jun. 26, 2012

(54) SUNSCREEN COMPOSITION WITH FATTY ACID ALKANOLAMIDES

(75) Inventors: Jack Polonka, Peekskill, NY (US); Luis Roberto Misso, Stratford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 367 days.

(21) Appl. No.: 12/611,943

(22) Filed: Nov. 4, 2009

(65) Prior Publication Data

US 2011/0104087 A1    May 5, 2011

(51) Int. Cl.
| | |
|---|---|
| A61K 8/42 | (2006.01) |
| A61Q 17/04 | (2006.01) |
| A01N 37/36 | (2006.01) |
| A01N 43/50 | (2006.01) |
| A01K 35/00 | (2006.01) |
| A01K 31/16 | (2006.01) |

(52) U.S. Cl. .............. 424/60; 424/59; 424/63; 514/159; 514/163; 514/686; 514/396; 514/613

(58) Field of Classification Search .................. None
See application file for complete search history.

(56) References Cited

U.S. PATENT DOCUMENTS

| | | | |
|---|---|---|---|
| 4,585,597 A | 4/1986 | Lang et al. | |
| 5,041,281 A | 8/1991 | Strobridge | |
| 5,099,013 A | 3/1992 | Balazs et al. | |
| 5,116,601 A | 5/1992 | Mondet et al. | |
| 5,182,407 A | 1/1993 | Sebag | |
| 5,470,551 A | 11/1995 | Dubief et al. | |
| 5,626,840 A | 5/1997 | Thomaides et al. | |
| 5,667,765 A | 9/1997 | Hansenne et al. | |
| 5,709,850 A | 1/1998 | Mondet et al. | |
| 5,753,215 A | 5/1998 | Mougin et al. | |
| 5,759,524 A | 6/1998 | Tanner et al. | |
| 5,830,438 A | 11/1998 | Dupuis | |
| 5,961,961 A | 10/1999 | Dobkowski et al. | |
| 5,968,494 A | 10/1999 | Kukkala et al. | |
| 6,036,945 A | 3/2000 | Deblasi et al. | |
| 6,083,492 A | 7/2000 | Modi | |
| 6,153,176 A | 11/2000 | Kaleta et al. | |
| 6,280,710 B1 | 8/2001 | Deblasi et al. | |
| 6,337,077 B1 | 1/2002 | Chevalier et al. | |
| 6,440,401 B1 | 8/2002 | Heywang et al. | |
| 6,485,713 B1 | 11/2002 | Bonda et al. | |
| 7,014,842 B2 | 3/2006 | Dueva-Koganov et al. | |
| 7,244,416 B2 | 7/2007 | Meyer et al. | |
| 7,465,460 B1 | 12/2008 | Gross | |
| 2002/0176834 A1 | 11/2002 | Adams et al. | |
| 2003/0114520 A1* | 6/2003 | Pereira et al. | 514/532 |
| 2003/0191271 A1 | 10/2003 | Mondet et al. | |
| 2004/0086470 A1* | 5/2004 | Nieendick et al. | 424/63 |
| 2004/0226815 A1 | 11/2004 | L'Alloret | |
| 2004/0228814 A1 | 11/2004 | Candau et al. | |
| 2004/0241112 A1 | 12/2004 | Evison et al. | |
| 2004/0258636 A1 | 12/2004 | Richard et al. | |
| 2005/0025736 A1 | 2/2005 | Jachowicz et al. | |
| 2007/0074356 A1 | 4/2007 | Lalleman | |
| 2007/0142255 A1 | 6/2007 | Qiu | |
| 2008/0181858 A1 | 7/2008 | Davis et al. | |
| 2008/0199526 A1 | 8/2008 | Poschalko et al. | |
| 2008/0287537 A1 | 11/2008 | Dalko | |

FOREIGN PATENT DOCUMENTS

| | | |
|---|---|---|
| EP | 1591099 A2 | 11/2005 |
| EP | 2025324 A1 | 2/2009 |
| WO | 90/00894 | 2/1990 |
| WO | 95/00106 | 1/1995 |
| WO | 97/46231 | 12/1997 |
| WO | 00/27353 | 5/2000 |
| WO | 01/05366 A1 | 1/2001 |
| WO | 2007/128776 A1 | 11/2007 |

OTHER PUBLICATIONS

Co-Pending Application—Misso et al.—Filed: Nov. 4, 2009; entitled Sunscreen Composition.
Co-Pending Application—Polonka et al.—Filed: Nov. 4, 2009; entitled Enhanced Photo Protection.
International Search Report PCT/EP2010/066183, dated Apr. 27, 2011.

* cited by examiner

*Primary Examiner* — Ernst Arnold
*Assistant Examiner* — Hong Yu
(74) *Attorney, Agent, or Firm* — Milton L. Honig

(57) ABSTRACT

A cosmetic composition is provided including a water-insoluble UV-A sunscreen agent having a $\lambda_{max}$ at 330-380 nm, a water-insoluble UV-B sunscreen agent having a $\lambda_{max}$ between 280 and 320 nm, and a water-soluble sunscreen agent having a $\lambda_{max}$ between 280 and 400 nm, in combination with a photo protective enhancing agent which is a stearyl alkanolamide of structure $R^1C(O)NR^2—R^3OH$ wherein $R^1$ is a $C_{17}$ radical, $R^2$ is hydrogen or a $C_1$-$C_6$ radical, and $R^3$ is a $C_2$-$C_8$ radical, in a cosmetically acceptable carrier.

6 Claims, No Drawings

SUNSCREEN COMPOSITION WITH FATTY ACID ALKANOLAMIDES

BACKGROUND OF THE INVENTION

1. Field of the Invention

The invention concerns cosmetic compositions with enhanced photoprotection properties.

2. The Related Art

Many people dislike northern climates. There is a longing to bask in the warmth of the sun. Days at the beach find us in swimsuit attire. Many seek to turn their pale winter skin into a bronzed appearance. Others of naturally darker skin simply enjoy the refreshment of the seashore. Without protection from harmful ultraviolet radiation damage, these pleasures can turn into premature aging. Skin can loose elasticity and wrinkles appear in the premature aging process. Radiation can promote erythemal damage, can cause photo allergic reactions, and is implicated in skin cancers.

Protective measures are necessary. Lotions and creams formulated with sunscreens can shield against ultraviolet damaging radiation. The extent of protection varies widely.

Numerous ultraviolet photoprotective (sunscreen) agents are known. Nonetheless, only a small number are both commercially available and approved by regulatory authorities. A need exists to operate with known approved commercial sunscreen agents yet formulating them to achieve more than their expected level of photoprotection.

Representative of the art is U.S. Pat. No. 5,961,961 (Dobkowski et al.) reporting enhancement of the photoprotective effect by utilizing relatively large particle size titanium dioxide coupled with an organic sunscreen agent. Representative organic sunscreen agents include Benzophenone-3, octyl salicylate, octyl methoxycinnamate and 2-phenylbenzimidazole-5-sulphonic acid.

Although the aforementioned technology is useful, there is a need to achieve higher photo protective efficacy for cosmetics.

SUMMARY OF THE INVENTION

A cosmetic composition is provided which includes:
(i) a water-insoluble UV-A sunscreen agent having a $\lambda_{max}$ ranging from 330 to 380 nm;
(ii) a water-insoluble UV-B sunscreen agent having a $\lambda_{max}$ between 280 and 320 nm;
(iii) a water-soluble sunscreen agent having a $\lambda_{max}$ between 280 and 400 nm; and
(iv) a photo protective enhancing agent having the structure

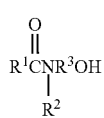

wherein $R^1$ is a $C_{17}$ radical, $R^2$ is hydrogen or a $C_1$-$C_6$ radical, and $R^3$ is a $C_2$-$C_8$ radical; and
(v) a cosmetically acceptable carrier.

DETAILED DESCRIPTION OF THE INVENTION

Now it has been found that photoprotection can be enhanced by utilizing a cocktail of three different types of sunscreen agents in combination with a photo protective enhancing agent which is a stearic alkanolamide.

The photo protective enhancing agents have the general structure as noted below.

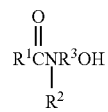

wherein $R^1$ is a $C_{17}$ radical, $R^2$ is hydrogen or a $C_1$-$C_6$ radical, and $R^3$ is a $C_2$-$C_8$ radical.

Particularly preferred embodiments are stearyl butanolamide, stearyl monoethanolamide, and stearyl monoisopropanolamide derivatives of stearic acids having the respective structures listed below

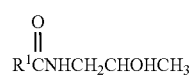

wherein $R^1C(O)$ is a stearyl radical.

Amounts of the stearoyl alkanolamides may range from about 0.05 to about 5%, preferably from about 0.09 to about 1%, and optimally from about 0.1 to about 0.5% by weight of a composition.

Cosmetic compositions of the present invention will include as a first element a water-insoluble UV-A sunscreen agent having a $\lambda_{max}$ between 330 and 380 nm. Particularly the $\lambda_{max}$ will range from 340 to 360 nm, and optimally at 360 nm. In this category of sunscreen agent, the preferred materials are 4,4'-t-butyl methoxydibenzoylmethane known as Avobenzone (available as Parsol 1789®), 2-hydroxy-4-methoxybenzophenone known as Benzophenone-3 and as Oxybenzone, terephthalylidene dicamphor sulfonic acid (available as Mexoryl SX) and combinations thereof.

Amounts of the water-insoluble UV-A sunscreen agent may range from 1 to 4%, optimally from 2 to 3% by weight of the composition.

A second element of the present invention is a water-insoluble UV-B sunscreen agent having a $\lambda_{max}$ ranging between 280 and 320 nm. More particularly the $\lambda_{max}$ may range from 300 to 310 nm, and optimally at 305 nm.

A large variety of substances may be utilized as the UV-B sunscreen agent. Illustrative are 2-ethylhexyl p-methoxycinnamate, octyldimethyl p-aminobenzoic acid, digalloyltrioleate, ethyl 4-[bis(hydroxypropyl)]aminobenzoate, 2-ethylhexyl-2-cyano-3,3-diphenylacrylate, octylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, bis-ethylhexyloxyphenol methoxyphenol triazine, methylene bis-benzotriazolyl tetramethylbutylphenol, dimethicodiethylbenzal malonate, isoamyl methoxycinnamate, octyl triazone, and mixtures thereof.

Amounts of the water-insoluble UV-B sunscreen agent may range from 1 to 8%, preferably from 3 to 6%, and optimally about 5% by weight of the composition. Most preferred is octyl salicylate.

Most preferred for purposes of this invention are compositions utilizing 3% Avobenzone and 4-5% octylsalicylate. Also useful is a combination of 2% Avobenzone and 5% octylsalicylate. These combinations are best joined with 2-phenylbenzimidazole-5-sulfonic acid or salts forms (available as Ensulizole®) in an amount of about 3%.

Advantageously but not necessarily the amount of water-insoluble UV-A to UV-B sunscreen agent may range from about 1:5 to 1:1, more preferably from 3:5 to 4:5 by weight of the composition.

A third type of photoprotection is provided by a water-soluble sunscreen agent having a $\lambda_{max}$ between 280 and 400 nm. Especially useful for this purpose is 2-phenylbenzimidazole-5-sulfonic acid and salt forms. Amounts of the water-soluble sunscreen agent may range from 1 to 4%, preferably from 2 to 3%, and optimally about 3% by weight of the composition.

When the water-soluble sunscreen agent is in salt form, advantageously the salt may be a metallic counter ion selected from sodium and potassium or an ammonium counter ion including triethanolammonium. Most preferred is a mixture of sodium and potassium counter ions, which when present may be found in a relative molar ratio sodium to potassium of 0.5:2 to 2:1, preferably 0.8:2 to 1.5:1, more preferably from 0.8:1 to 1:1.

Cosmetic compositions of the present invention may be in cream or lotion form. These will feature a cosmetically acceptable carrier.

Carriers may be present in amounts ranging from about 5 to about 98%, preferably from about 20 to about 95%, optimally from about 40 to about 80% by weight of the cosmetic compositions. Water is the most common carrier for this invention. Oily carriers in the presence of water and an emulsifier will form emulsion systems as carriers. These systems may either be water-in-oil or oil-in-water emulsions. Besides water, suitable carrier classes include fatty acids, silicones, polyhydric alcohols, fatty alcohols, hydrocarbons, triglycerides and thickening powders.

Fatty acids may be selected from stearic acid, oleic acid, linoleic acid, linolinic acid, lauric acid, myristic acid, palmitic acid, behenic acid and mixtures thereof. Amounts may range from 1 to 50%, preferably from 8 to 30%, and optimally from 10 to 25% by weight of the composition.

Concentrations of the silicone may range from about 5% to about 60%, more preferably from about 5% to about 40%, by weight of the composition. These silicone fluids may be organic, silicone-containing or fluorine-containing, volatile or non-volatile, polar or non-polar.

Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.

Hydrocarbons may be useful as cosmetically acceptable carriers for compositions of this invention. They may include mineral oil, petrolatum and polyalpha-olefins. Examples of preferred volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals).

Polyhydric alcohols may serve as carriers. Illustrative of this group are propylyene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin.

Fatty alcohols may also be useful carriers. The term "fatty" refers to carbon chain lengths ranging from 10 to 30 carbon atoms. Illustrative of this category are lauryl alcohol, cetyl alcohol, stearyl alcohol, isostearyl alcohol and combinations thereof.

Triglycerides are another group of materials useful as carriers. Illustrative but not limiting are sunflower seed oil, cotton oil, canola oil, soybean oil, castor oil, borage oil, olive oil, shea butter, jojoba oil and mixtures thereof. Mono- and diglycerides may also be useful. Illustrative of these categories are glyceryl monostearate and glyceryl distearate.

The carriers can comprise one or more thickening agents, preferably from about 0.05% to about 10%, more preferably from about 0.1% to about 5%, and even more preferably from about 0.25% to about 4%, by weight for the composition.

Advantageously in some embodiments, the carrier may include or completely be a crystalline gel structurant comprising a surfactant and co-surfactant. The nature of the surfactant and co-surfactant will depend upon whether the crystalline gel structurant is anionic or nonionic. For structurants that are anionic, the preferred surfactants are $C_{10}$-$C_{22}$ fatty acids and salts (i.e. soap) thereof and particularly combinations of these materials. Typical counterions forming the fatty acid salt are those of ammonium, sodium, potassium, lithium, trialkanolammonium (e.g. triethanolammonium) and combinations thereof. Amounts of the fatty acid to the fatty acid salt when both present may range from about 100:1 to about 1:100, preferably from about 50:1 to about 1:50, and optimally from about 3:1 to about 1:3 by weight. Illustrative fatty acids include behenic acid, stearic acid, isostearic acid, myristic acid, lauric acid, oleic acid, hydroxystearic acid and combinations thereof. Most preferred is stearic acid.

The co-surfactant for an anionic crystalline gel structurant typically is a $C_{10}$-$C_{22}$ fatty alcohol, a $C_1$-$C_{200}$ ester of a $C_{10}$-$C_{22}$ fatty acid and particularly combinations of these materials. Relative amounts of the ester to the alcohol when both present may range from about 100:1 to about 1:100, preferably from about 50:1 to about 1:50, and optimally from about 3:1 to about 1:3 by weight. Typical fatty alcohols include behenyl alcohol, stearyl alcohol, cetyl alcohol, myristyl alcohol, lauryl alcohol, oleyl alcohol and combinations thereof. Esters of the fatty acid preferably are polyol esters such as $C_2$-$C_3$ alkoxylated alcohol esters. Among these are the polyethoxy, polypropoxy and block polyethyoxy/polypropoxy alcohol esters. Particularly preferred are such esters as PEG-100 stearate, PEG-20 stearate, PEG-80 laurate, PEG-20 laurate, PEG-100 palmitate, PEG-20 palmitate and combinations thereof.

The relative amount of surfactant and co-surfactant for the anionic structurant may range from about 50:1 to about 1:50, preferably from about 10:1 to about 1:10, and optimally from about 3:1 to about 1:3 by weight.

Nonionic type crystalline gel structurant will have a surfactant and a co-surfactant different than that for the anionic systems. Preferred nonionic structurant surfactants are $C_1$-$C_{200}$ esters of $C_{10}$-$C_{22}$ fatty acid. Esters of the fatty acid preferably are polyol esters such as $C_2$-$C_3$ alkoxylated alcohol esters. Among these are the polyethoxy, polypropoxy and block polyethyoxy/polypropoxy alcohol esters. Particularly preferred are such esters as PEG-100 stearate, PEG-20 stearate, PEG-80 laurate, PEG-20 laurate, PEG-100 palmitate, PEG-20 palmitate and combinations thereof.

The co-surfactant of a nonionic structurant typically may be a combination of a $C_{10}$-$C_{22}$ fatty alcohol, glyceryl esters of a $C_{10}$-$C_{22}$ fatty acid, and a $C_{10}$-$C_{22}$ unesterified fatty acid. Relative amounts of the ester to the alcohol may range from about 100:1 to about 1:100, preferably from about 50:1 to about 1:50, and optimally from about 3:1 to about 1:3 by weight. Relative amounts of the combination of glyceryl ester and fatty alcohol to unesterified fatty acid may range from about 100:1 to about 1:100, preferably from about 50:1 to about 1:50, and optimally from about 3:1 to about 1:3 by weight. Typical fatty alcohols include behenyl alcohol, stearyl alcohol, cetyl alcohol, myristyl alcohol, lauryl alcohol, oleyl alcohol and combinations thereof.

The relative amount of surfactant and co-surfactant in a nonionic structurant may range from about 50:1 to about 1:50, preferably from about 10:1 to about 1:10, and optimally from about 3:1 to about 1:3 by weight.

Cosmetic compositions of the present invention may contain a variety of optional components to enhance physical properties and performance.

The optional components, when incorporated into the cosmetic compositions, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these classes include: abrasives, absorbents, aesthetic components such as fragrances, pigments, colorings/colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents, antioxidants, biological additives, buffering agents, bulking agents, chelating agents, chemical additives, colorants, cosmetic astringents, cosmetic biocides, denaturants, drug astringents, external analgesics, film forming polymers, opacifying agents, pH adjusters, propellants, reducing agents, sequestrants, skin bleaching and lightening agents, skin conditioning agents, skin soothing and/or healing agents and derivatives, skin treating agents, thickeners, and vitamins and derivatives thereof.

A safe and effective amount of an anti-oxidant/radical scavenger may be added in amounts from about 0.01% to about 10%, more preferably from about 0.1% to about 5% by weight of the composition.

Anti-oxidants/radical scavengers may be employed such as ascorbic acid (vitamin C) and its salts, ascorbyl esters of fatty acids, ascorbic acid derivatives (e.g. magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolor®), amines (e.g. N,N-diethylhydroxylamine, amino-guanidine), nordihydroguaiaretic acid, bioflavonoids, amino acids, cassia plant and extracts, silymarin, tea extracts, and grape skin/seed extracts. Preferred anti-oxidants/radical scavengers are selected from esters of tocopherol, more preferably tocopherol acetate.

The cosmetic compositions may optionally comprise a flavonoid compound. Flavonoids are disclosed in U.S. Pat. Nos. 5,686,082 and 5,686,367 herein incorporated by reference. Examples of flavonoids particularly suitable flavones, isoflavones, coumarins, chromones, discoumarols, chromanones, chromanols, isomers (e.g. cis/trans isomers) thereof, and mixtures thereof.

Preferred for use are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Stearloids, Inc., and Aldrich Chemical Company, Inc. The herein described flavonoid compounds are preferably present in from about 0.01% to about 20%, more preferably from about 0.1% to about 10%, and even more preferably from about 0.5% to about 5% by weight.

Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g. salts and esters).

The compositions may comprise a tanning active. When present, it is preferable that the compositions comprise from about 0.1% to about 20%, more preferably from about 2% to about 7% by weight of the composition. A preferred tanning active is dihydroxyacetone.

The compositions may comprise a skin lightening agent. When used, the compositions preferably comprise from about 0.1% to about 10%, more preferably from about 0.2% to about 5%, also preferably from about 0.5% to about 2%, by weight of the composition, of a skin lightening agent. Suitable skin lightening agents include niacinamide, kojic acid, arbutin, tranexamic acid, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract).

The compositions may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and even more preferably from about 0.05% to about 2% by weight of the composition.

Preferred examples of these actives include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cystein, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, climbazole, miconazole, ketoconazole, neocycin sulfate, and mixtures thereof.

The compositions may comprise a conditioning agent selected from the group consisting of humectants, moisturizers, or skin conditioners. A variety of these materials can be employed and each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol and hexylene glycol; polyethylene glycols; sugars and starch derivatives (e.g. alkoxylated glucose, fructose, sucrose, trehalose); hyaluronic acid; lactamide monoethanolamine; acetamide monoethanolamine; sucrose polyester; petrolatum; and mixtures thereof.

The cosmetic compositions include but are not limited to lotions, milks, mousses, serums, sprays, aerosols, foams, sticks, pencils, gels, creams and ointments. The compositions may also be applied via a woven or nonwoven synthetic and/or natural fibered textile (wipe or towelette).

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLES 1-8

A series of compositions are outlined in Table I which are illustrative of the present invention.

EXAMPLE 9

Photoprotective effects were evaluated on a model system wherein the lamellar oil phase of an aqueous emulsion had the formula outlined in Table II.

TABLE II

| Component | Weight % As Active |
|---|---|
| Stearic Acid | 1.58 |
| Glyceryl Monostearate | 0.81 |
| Cetyl Alcohol | 0.47 |
| PEG-100 Stearate | 1.50 |
| Avobenzone | 3.00 |
| Octyl Salicylate | 5.00 |
| 2-Phenylbenzimidazole-5-sulfonic salt (in aqueous phase) | 1.00 |
| Stearyl Butanolamide or Stearyl Ethanolamide | * |

*amount of the alkanolamide is a variable according to Table III; the alkanolamide is dissolved in glycol stearate as solvent.

Procedure

SPF Measurements

Sun protection factor (SPF) was measured in vitro using an Optometrics SPF 290 instrument. The test procedure required calibration of the monochrometer and sample stage of the Optometrics SPF 290 instrument. Thereafter the instrument was calibrated with a blank sample quartz plate (10 cm×10 cm and 3 mm thickness). Calibration zeros the UV detector. Formulas were applied and spread uniformly onto a plate to leave a film of 2 mg/cm$^2$. The film was left to dry for 30 minutes. Subsequently an SPF reading was taken on the dried film using three measurements on different parts of the coated quartz plate and recording an average value.

MPF is equivalent to the SPF value at a specific wavelength. For the present experiments the wavelength is the peak maximum at 305 to 360 nm.

TABLE I

| | Sample No. (Weight %) | | | | | | | |
|---|---|---|---|---|---|---|---|---|
| Component | 1 | 2 | 3 | 4 | 5 | 6 | 7 | 8 |
| Stearic Acid | 15.0 | 15.0 | 5.0 | 10.0 | 10.0 | 8.0 | 8.0 | 8.0 |
| Glycol Stearate | 8.0 | 8.0 | 5.0 | 5.0 | 8.0 | 8.0 | 8.0 | 8.0 |
| Glycerol Monostearate | 2.5 | 4.5 | 1.5 | 1.5 | 2.5 | 2.5 | 2.5 | 2.5 |
| Cetyl Alcohol | 1.5 | 0.5 | 0.5 | 1.0 | 1.0 | 1.0 | 1.0 | 1.0 |
| PEG-100 Stearate | 1.5 | 2.5 | 1.5 | 2.5 | 2.5 | 2.5 | 1.5 | 1.5 |
| Potassium Stearate | 1.0 | 1.5 | 0.8 | 0.8 | 3.0 | 1.5 | 1.5 | 1.1 |
| Avobenzone | 2.0 | 2.0 | 3.0 | 3.0 | 2.0 | 2.0 | 3.0 | 3.0 |
| Octyl Salicylate | 5.0 | 5.0 | 5.0 | 5.0 | 5.0 | 5.0 | 5.0 | 5.0 |
| 2-Phenylbenzimidazole-5-sulfonate salt | 1.2 | 1.2 | 1.2 | 0.9 | 1.2 | 1.2 | 1.5 | 1.0 |
| Stearyl Butanolamide | 0.05 | 0.1 | 0.2 | 0.4 | 0.5 | 0.6 | 0.07 | 0.15 |
| Glycerin | 5.0 | 5.0 | 5.0 | 5.0 | 5.0 | 5.0 | 5.0 | 5.0 |
| Silicone Oil | 0.5 | 0.5 | 0.5 | 0.5 | 0.5 | 0.5 | 0.5 | 0.5 |
| Isopropyl Myristate | 0.75 | 0.75 | 0.75 | 0.75 | 0.75 | 0.75 | 0.75 | 0.75 |
| Methyl Paraben | 0.15 | 0.15 | 0.15 | 0.15 | 0.15 | 0.15 | 0.15 | 0.15 |
| Propyl Paraben | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 |

Results

Table III outlines the effects of the photo protective enhancing agent within the context of the Table II formula.

TABLE III

| | Enhancing Agent* (Weight %) | UV Absorption Data | | |
|---|---|---|---|---|
| Sample | | In-vitro SPF | Intensity $\lambda_{max}$ = 305 nm (MPF) | Intensity $\lambda_{max}$ = 360 nm (MPF) |
| 1 | 0.009 | 25.4 | 53.3 | 18.2 |
| 2 | 0.09 | 28.2 | 56.1 | 34.2 |
| 3 | 0.174 | 33.6 | 66.0 | 42.3 |
| 4 | 0.348 | 33.4 | 59.7 | 48.3 |
| 5 | 0.522 | 31.3 | 60.3 | 42.2 |
| 6 | 0.174 | 30.7 | 52.4 | 41.1 |

*stearyl butanolamide except Sample 6 which uses stearyl ethanolamide

A primary effect of the enhancing agent was upon increasing intensities at $\lambda_{max}$ 360 nm. Sample 1 which only had a very small amount of the enhancing agent (0.009%) delivered a $\lambda_{max}$ 360 nm intensity of 18.2. Sample 2 increased the level of the enhancing agent ten-fold to 0.09% resulting in a substantial intensity increase at $\lambda_{max}$ 360 nm to a 34.2 value. Improvements in the in-vitro SPF was also evident (note rise from 25.4 to 28.2, respectively). Effects of the enhancing agent in this system appear to be maximum around 0.4-0.5% active as seen in Samples 4 and 5.

What is claimed is:

1. A cosmetic composition comprising:
   (i) from 1 to 4% by weight of the composition of a water-insoluble UV-A sunscreen agent having a $\lambda_{max}$ ranging from 330 to 380 nm which is Avobenzone;
   (ii) from 1 to 8% by weight of the composition of a water-insoluble UV-B sunscreen agent having a $\lambda_{max}$ between 280 and 320 nm which is octyl salicylate;
   (iii) from 1 to 3% by weight of the composition of a water-soluble sunscreen agent having a $\lambda_{max}$ between 280 and 400 nm which is 2-phenylbenzimidizole-5-sulfonic acid or salt thereof; and
   (iv) from 0.05 to 5% by weight of the composition of a photo protective enhancing agent having the structure

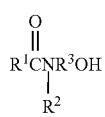
   (I)

wherein $R^1$ is a $C_{17}$ radical, $R^2$ is hydrogen or a $C_1$-$C_6$ radical, and $R^3$ is a $C_2$-$C_8$ radical; and
   (v) a cosmetically acceptable carrier, and wherein the composition achieves an in-vitro SPF higher than 25.4.

2. The composition according to claim 1 wherein the photo protective enhancing agent has a structure selected from the group consisting of:

   (II)

   (III)

   (IV)

wherein $R^1C(O)$ group is a stearyl radical.

3. The composition according to claim 1 wherein the photo protective enhancing agent is present in an amount from about 0.09 to about 1% by weight of the composition.

4. A composition according to claim 1 wherein the photo protective enhancing agent is stearyl butanolamide.

5. A composition according to claim 1 wherein the photo protective enhancing agent is stearyl monoethanolamide.

6. The composition according to claim 1 wherein the photo protective enhancing agent is present in an amount from about 0.1 to about 0.5% by weight of the composition.

* * * * *